US 11,998,243 B2
Jun. 4, 2024

(12) United States Patent
Bobbitt et al.

(54) SPINAL IMPLANT SYSTEM AND METHOD

(71) Applicant: WARSAW ORTHOPEDIC INC., Warsaw, IN (US)

(72) Inventors: Dustin Bobbitt, Hernando, MS (US); Rex W. Armstrong, Cordova, TN (US); David A. Mire, Cordova, TN (US); William Alan Rezach, Covington, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 423 days.

(21) Appl. No.: 16/919,335

(22) Filed: Jul. 2, 2020

(65) Prior Publication Data
US 2020/0330133 A1 Oct. 22, 2020

Related U.S. Application Data

(63) Continuation of application No. 15/441,774, filed on Feb. 24, 2017, now Pat. No. 10,736,665.

(51) Int. Cl.
*A61B 17/70* (2006.01)
*A61B 17/86* (2006.01)
*A61B 90/00* (2016.01)

(52) U.S. Cl.
CPC ...... *A61B 17/7032* (2013.01); *A61B 17/7001* (2013.01); *A61B 17/7037* (2013.01); *A61B 17/7038* (2013.01); *A61B 17/7049* (2013.01); *A61B 17/8605* (2013.01); *A61B 17/8685* (2013.01); *A61B 2090/037* (2016.02)

(58) Field of Classification Search
CPC ............ A61B 17/7001; A61B 17/7032; A61B 17/7037; A61B 17/7038; A61B 17/7049; A61B 17/8605; A61B 17/8685; A61B 2090/037
See application file for complete search history.

(56) References Cited

U.S. PATENT DOCUMENTS

| 5,885,286 A | 3/1999 | Sherman et al. |
| 6,565,566 B1 | 5/2003 | Wagner et al. |
| 8,034,089 B2 | 10/2011 | Matthis et al. |
| 8,097,025 B2 | 1/2012 | Hawkes et al. |
| 8,167,910 B2 | 5/2012 | Nilsson |
| 8,197,518 B2 | 6/2012 | Hammill, Sr. et al. |
| 8,298,265 B2 | 10/2012 | Purcell et al. |

(Continued)

OTHER PUBLICATIONS

European Patent Office, Berlin, Germany, Communication pursuant to Article 94(3) EPC, European Patent Application 18 154 386.9 dated Oct. 27, 2020.

(Continued)

*Primary Examiner* — Nicholas J Plionis
(74) *Attorney, Agent, or Firm* — Sorell, Lenna & Schmidt, LLP

(57) ABSTRACT

A bone fastener comprises a head including a first receiver that defines an implant cavity and a second receiver that defines an implant cavity. The first receiver is connected to the second receiver. A shaft is aligned with the first receiver and configured to engage tissue. A part is disposed within the implant cavity of the second receiver and movable relative thereto in a selected plane of a body. Systems, surgical instruments, spinal constructs, implants and methods are disclosed.

23 Claims, 5 Drawing Sheets

(56) References Cited

U.S. PATENT DOCUMENTS

| | | |
|---|---|---|
| 8,298,275 B2 | 10/2012 | Rezach et al. |
| 2004/0111088 A1* | 6/2004 | Picetti ................ A61B 17/7037 606/279 |
| 2007/0250061 A1 | 10/2007 | Chin et al. |
| 2007/0270839 A1 | 11/2007 | Jeon et al. |
| 2008/0119850 A1* | 5/2008 | Sicvol ................ A61B 17/7037 606/306 |
| 2011/0093021 A1 | 4/2011 | Fanger et al. |
| 2011/0106166 A1 | 5/2011 | Keyer et al. |
| 2011/0106173 A1 | 5/2011 | Lindemann et al. |
| 2011/0106175 A1 | 5/2011 | Rezach |
| 2011/0257690 A1* | 10/2011 | Rezach ............. A61B 17/7037 606/302 |
| 2012/0123486 A1* | 5/2012 | Werner ............. A61B 17/7037 606/308 |
| 2014/0018858 A1* | 1/2014 | Laeng ................ A61B 17/7044 606/267 |
| 2014/0135839 A1 | 5/2014 | Frankel et al. |
| 2015/0223844 A1 | 8/2015 | Leff et al. |
| 2015/0359568 A1 | 12/2015 | Rezach |
| 2018/0228518 A1* | 8/2018 | Carruth ............. A61B 17/7049 |

OTHER PUBLICATIONS

China National Intellectual Property Administration, Application/Patent No. 201810128225.3, Notice on the First Office Action, dated Apr. 18, 2022.

\* cited by examiner

SPINAL IMPLANT SYSTEM AND METHOD

CROSS-REFERENCE TO RELATED APPLICATION

This application is a divisional of U.S. patent application Ser. No. 15/441,774, filed Feb. 24, 2017, which is expressly incorporated herein by reference, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener comprises a head including a first receiver that defines an implant cavity and a second receiver that defines an implant cavity. The first receiver is connected to the second receiver. A shaft is aligned with the first receiver and configured to engage tissue. A part is disposed within the implant cavity of the second receiver and movable relative thereto in a selected plane of a body. In some embodiments, systems, surgical instruments, spinal constructs, implants and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
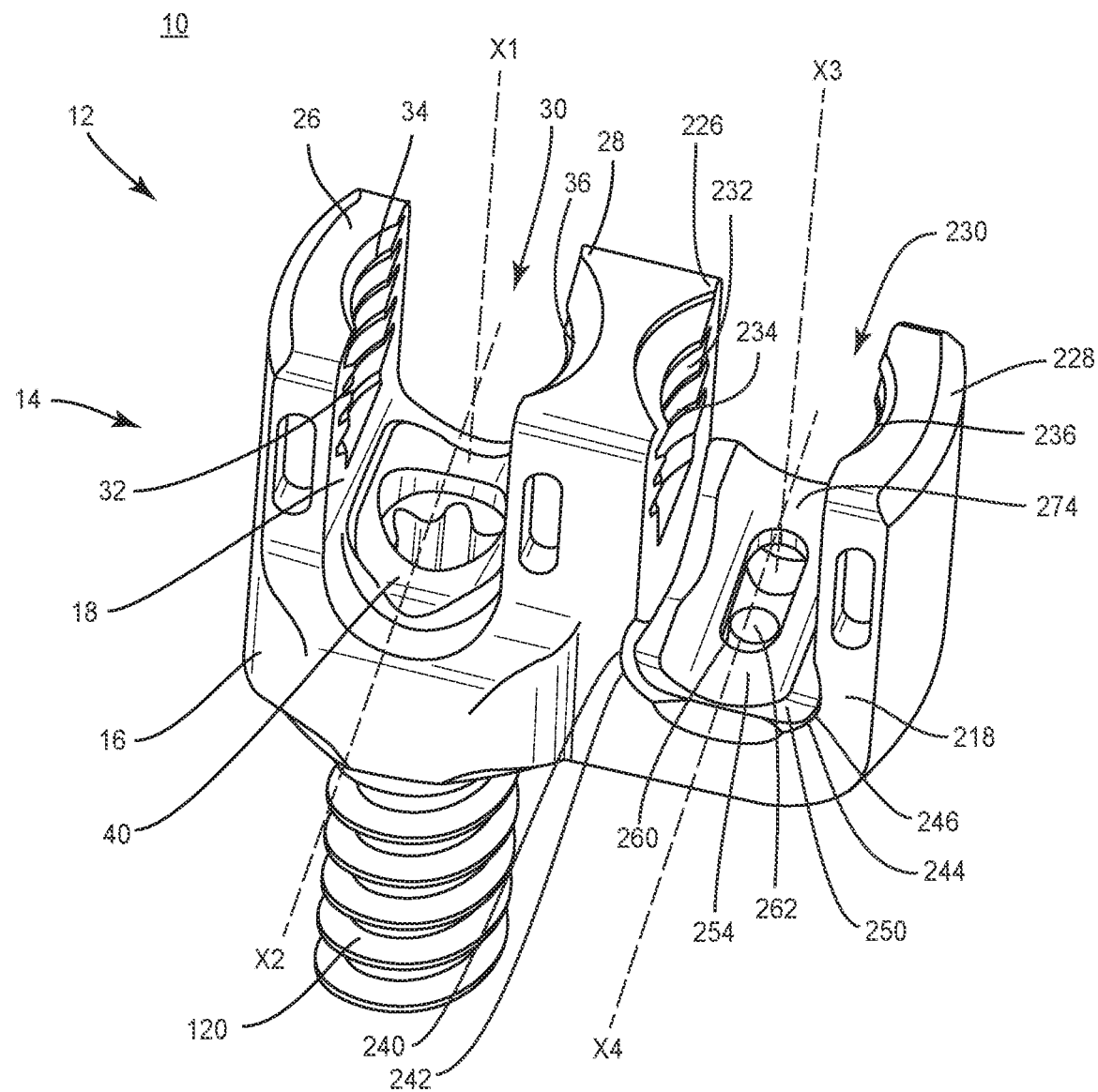
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a fastener having a first implant cavity and a second implant cavity. In some embodiments, the present surgical system includes a spinal construct having a dual rod multi axial screw with a primary rod slot and a secondary rod slot. In some embodiments, the secondary rod slot includes a sagittal adjusting saddle. In some embodiments, the secondary rod slot is configured to accommodate sagittal angulation of a second rod as a screw head position is locked when a first rod is attached. In some embodiments, the sagittal angulation of the secondary rod slot is configured to increase construct performance. In some embodiments, the present surgical system includes a spinal construct having a fastener that supports one or more spinal rods in a configuration to facilitate stabilization of vertebrae.

In some embodiments, one or more implant cavities of the fastener includes a saddle that is configured for engagement with grooves of the implant cavity for movement along a selected path. In some embodiments, one or more rod slots include a saddle configured for engagement with grooves disposed with the rod slot. In some embodiments, a rod slot includes a pin configured to retain the saddle for relative movement. In some embodiments, the fastener includes a fixed axis screw having a sagittal adjusting saddle in a primary rod slot and/or a secondary rod slot. In some embodiments, the bone screw includes reduction tabs disposed with a primary rod slot and/or a secondary rod slot.

In some embodiments, the fastener includes a first rod slot aligned with a bone screw shaft and a second rod slot connected with the first slot. In some embodiments, the second rod slot is disposed in a parallel and adjacent orientation relative to the first rod slot. In some embodiments, the second rod slot is disposed in an angled and adjacent orientation relative to the first rod slot. In some embodiments, the second rod slot is disposed in a parallel and offset orientation relative to the first rod slot. In some embodiments, the second rod slot is disposed in an angled and offset orientation relative to the first rod slot.

In some embodiments, the first rod slot and/or the second rod slot can be connected with the bone screw shaft in a multi axial screw configuration, a fixed angle screw configuration or a sagittal adjusting screw configuration. In some embodiments, the fastener includes a reduction head having extended tabs that define the first rod slot and can be connected with a bone screw shaft in a multi axial screw configuration, a fixed angle screw configuration or a sagittal adjusting screw configuration. In some embodiments, the fastener includes a saddle disposed for movement with the first rod slot and/or the second rod slot in a multi axial screw configuration, a fixed angle screw configuration or a sagittal adjusting screw configuration. In some embodiments, the fastener includes a reduction head having extended tabs that define the first rod slot and/or the second rod slot and a saddle disposed for movement with the first rod slot and/or the second rod slot in a multi axial screw configuration, a fixed angle screw configuration or a sagittal adjusting screw configuration.

In one example, a fastener including parallel and adjacent rod slots can have a primary rod slot aligned with a multi axial, fixed angle or sagittal adjusting screw and a secondary rod slot having a multi axial, fixed angle or sagittal adjusting saddle. In one example, a fastener including angled and adjacent rod slots can have a primary rod slot aligned with a multi axial, fixed angle or sagittal adjusting screw and a secondary rod slot having a multi axial, fixed angle or sagittal adjusting saddle. In one example, a fastener including parallel and offset rod slots can have a primary rod slot aligned with a multi axial, fixed angle or sagittal adjusting screw and a secondary rod slot having a multi axial, fixed angle or sagittal adjusting saddle. In one example, a fastener including angled and offset rod slots can have a primary rod slot aligned with a multi axial, fixed angle or sagittal adjusting screw and a secondary rod slot having a multi axial, fixed angle or sagittal adjusting saddle. In some embodiments, the fastener includes a reduction head having extended tabs that define the primary rod slot and/or the secondary rod slot.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

Figure 2:
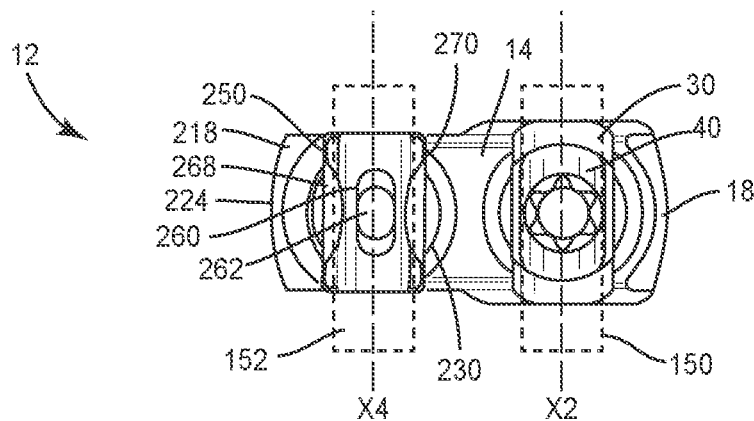
FIG. 2 is a plan view of the components shown in FIG. 1.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1 and 2, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites.

For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 comprises a bone fastener 12. Bone fastener 12 includes a head 14 and a shaft 120. Head 14 and shaft 120 are attached in a multi-axial screw configuration. In some embodiments, head 14 is selectively moveable along a plurality of axes relative to shaft 120 in a multi-axial configuration to accommodate connection with one or more spinal rods, as described herein.

In some embodiments, head 14 is selectively movable relative to shaft 120 through an angular range and disposable at a selected angle relative to shaft 120. In some embodiments, head 14 is selectively movable relative to shaft 120 through an angular range of 0-180 degrees. In some embodiments, the selected movement of head 14 includes rotation and/or pivotal movement of head 14 relative to shaft 120 about one or a plurality of axes. In some embodiments, the selected movement of head 14 includes rotation and/or pivotal movement of head 14 relative to shaft 120 through one or a plurality of planes. In some embodiments, the selected movement includes movement through one or more of transverse, vertical, horizontal, diagonal, coronal and/or sagittal planes of a body. In some embodiments, head 14 is disposed in a fixed orientation relative to shaft 120.

Head 14 includes a body 16. Body 16 includes a surface that defines a receiver 18. Receiver 18 is disposed in axial alignment with a head or connecting portion of shaft 120. Receiver 18 defines an axis X1 and includes an arm 26 and a portion 28 of an intermediate arm of head 14. Arm 26 and portion 28 are spaced apart. In some embodiments, shaft 120 is selectively movable relative to receiver 18 and/or axis X1 through an angular range and disposable at a selected angle relative to receiver 18 and/or axis X1, similar to that described herein. In some embodiments, all or only a portion of head 14 may have alternate cross section configurations, such as, for example, closed, V-shaped, ω-shaped, W-shaped, oval, oblong triangular, square, polygonal, irregular, uniform, non-uniform, offset, staggered, and/or tapered.

Arm 26 and portion 28 define an implant cavity, such as, for example, a rod slot 30 therebetween. Rod slot 30 is configured for top loading of a spinal implant, such as, for example, a spinal rod 150, as shown in FIG. 2. In some embodiments, rod slot 30 is configured for side loading or has a closed configuration. Arm 26 and portion 28 each extend parallel to axis X1, as shown in FIG. 1. In some embodiments, arm 26 and/or portion 28 may be disposed at alternate orientations, relative to axis X1, such as, for example, transverse, perpendicular and/or other angular orientations such as acute or obtuse, coaxial and/or may be offset or staggered. Arm 26 and portion 28 each include an arcuate outer surface extending between a pair of side surfaces. In some embodiments, at least one of the outer surfaces and the side surfaces of arm 26 and portion 28 have at least one recess or cavity therein configured to receive an insertion tool, compression instrument and/or surgical instruments for manipulating bone fastener 12.

Rod slot 30 is substantially U-shaped. Rod slot 30 defines and extends along an axis X2 oriented transverse to axis X1. In some embodiments, all or only a portion of rod slot 30 may have alternate cross section configurations, such as, for example, closed, V-shaped, ω-shaped, W-shaped, oval, oblong triangular, square, polygonal, irregular, uniform, non-uniform, offset, staggered, and/or tapered. Receiver 18 includes an inner surface 32. A portion of surface 32 includes a thread form 34 located adjacent arm 26 and a thread form 36 located adjacent portion 28. Thread forms 34, 36 are each configured for engagement with a coupling member, such as, for example, a set screw (not shown), to retain a spinal rod within rod slot 30. In some embodiments, surface 32 may be disposed with a set screw in alternate fixation configurations, such as, for example, friction fit, pressure fit, locking protrusion/recess, locking keyway and/or adhesive. In some embodiments, all or only a portion of surface 32 may have alternate surface configurations to enhance engagement with a spinal rod and/or a set screw such as, for example, rough, arcuate, undulating, mesh, porous, semi-porous, dimpled and/or textured.

Receiver 18 includes a crown 40. Crown 40 is configured to facilitate engagement of spinal rod 150 with receiver 18. In some embodiments, crown 40 includes a concave or semi-spherical configuration to accommodate the outer surface of a portion of shaft 120 such that head 14 is rotatable relative to shaft 120 in a multi-axial configuration, as described herein. In some embodiments, a set screw is configured for engagement with spinal rod 150 to facilitate fixation and/or locking of spinal rod 150 with receiver 18. The set screw is disposable with receiver 18 between a non-locking orientation, such that spinal rod 150 is translatable relative to bone fastener 12 and a locked orientation, including provisional and permanent fixation, such that the set screw fixes spinal rod 150 with bone fastener 12.

Head 14 includes a receiver 218, similar to receiver 18, described herein. Receiver 218 defines an axis X3 and includes arm 228 and a portion 226 of the intermediate arm of head 14. In some embodiments, shaft 120 is selectively movable relative to receiver 218 and/or axis X3 through an angular range and disposable at a selected angle relative to receiver 218 and/or axis X3, similar to that described herein.

Arm 228 and portion 226 are spaced apart to define a rod slot 230 therebetween. Portions 28, 226 are monolithically formed. Receiver 18 is connected to receiver 218 via head 14 and portions 28, 226 in a side by side and/or relatively parallel and adjacent orientation. As such, rod slots 30, 230 are disposed in a side by side and/or relatively parallel and adjacent orientation, and axes X2, X4 are disposed in a relatively parallel orientation, for corresponding disposal of spinal rods therein, as shown in FIG. 2. In some embodiments, portions 28, 226 are spaced apart.

Rod slot 230 is configured for top loading of a spinal rod 152, as shown in FIG. 2. Arms 228 and portion 226 each extend parallel to axis X3. In some embodiments, receivers 18, 218 form a ω-shaped cross section configuration of head 14. In some embodiments, receiver 218 is disposed separate and spaced apart from receiver 18. In some embodiments, receiver 218 may be disposed in various orientations, such as, for example, perpendicular, transverse and/or at angular orientations, such as acute or obtuse relative to receiver 18. In some embodiments, receiver 218 may be disposed offset or staggered relative to receiver 18, as described herein.

Rod slot 230 is disposed separate and apart from rod slot 30, and is substantially U-shaped. Rod slot 230 defines and extends along an axis X4 oriented parallel to axis X2. In some embodiments, all or only a portion of rod slot 230 may have alternate cross section configurations, such as, for example, closed, V-shaped, ω-shaped, W-shaped, oval, oblong triangular, square, polygonal, irregular, uniform, non-uniform, offset, staggered, and/or tapered. In some embodiments, rod slot 230 may be disposed in various orientations, such as, for example, perpendicular, transverse and/or at angular orientations, such as acute or obtuse, relative to rod slot 30.

Figure 3:
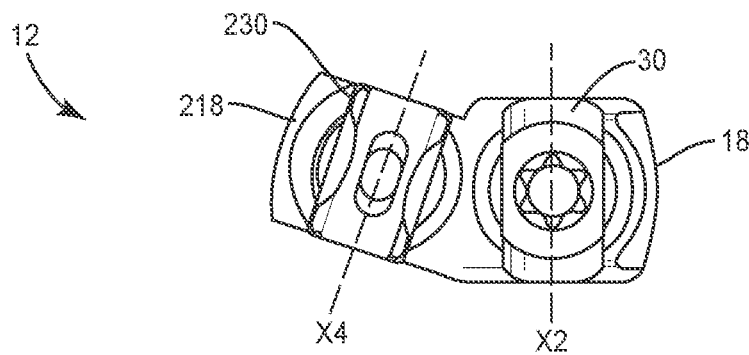
FIG. 3 is a plan view of components of one embodiment of a system in accordance with the principles of the present disclosure.
Figure 4:
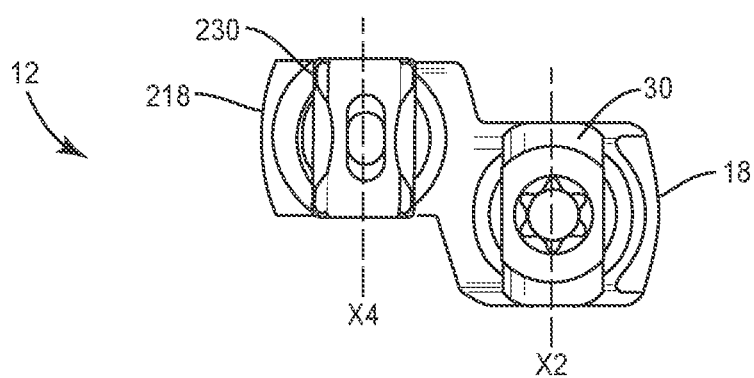
FIG. 4 is a plan view of components of one embodiment of a system in accordance with the principles of the present disclosure.
Figure 5:
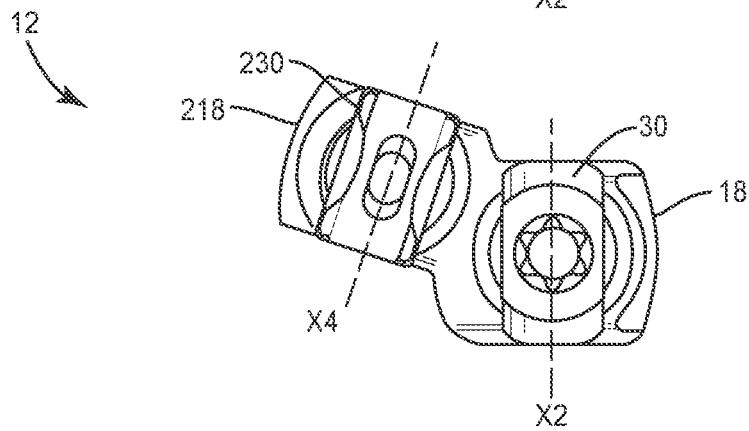
FIG. 5 is a plan view of components of one embodiment of a system in accordance with the principles of the present disclosure.

In some embodiments, receiver 218 is connected with receiver 18 in a relatively angled and adjacent orientation such that rod slots 30, 230 and axes X2, X4 are disposed in a relatively angled orientation for corresponding disposal of spinal rods therein, as shown in FIG. 3. In some embodiments, receiver 218 is connected to receiver 18 in a relatively angled and adjacent orientation such that axis X4 is disposed at a selected angle relative to axis X2 in an angular range of 0 to 45 degrees. In some embodiments, receiver 218 is connected with receiver 18 in a relatively parallel and offset orientation such that rod slots 30, 230 are disposed in a relatively parallel and offset orientation for corresponding disposal of spinal rods therein, as shown in FIG. 4. In some embodiments, receiver 218 is connected with receiver 18 in a relatively angled and offset orientation such that rod slots 30, 230 and axes X2, X4 are disposed in a corresponding orientation for disposal of spinal rods therein, as shown in FIG. 5. In some embodiments, receiver 218 is connected to receiver 18 in a relatively angled and offset orientation such that axis X4 is disposed at a selected angle relative to axis X2 in an angular range of 0 to 45 degrees.

Receiver 218 includes an inner surface 232. A portion of surface 232 includes a thread form 234 located adjacent portion 226 and a thread form 236 located adjacent arm 228. Thread forms 234, 236 are each configured for engagement with a coupling member, such as, for example, a set screw (not shown), to retain a spinal rod 152 within rod slot 230.

Portion 226 and arm 228 are configured to support relative movement of a saddle 250, as described herein. Portion 226 includes a surface 240 that defines a track 242 adjacent portion 226. Arm 228 includes a surface 244 that defines a track 246 adjacent arm 228. Tracks 242, 246 are configured to facilitate translation of saddle 250 relative to receiver 218, as described herein. Portion 226 and arm 228 are configured to guide saddle 250 along tracks 242, 246 relative to receiver 218. Receiver 218 includes an arcuate portion 254 configured for disposal of at least a portion of spinal rod 152, which may be positioned with receiver 218.

Saddle 250 includes a wall 268 and a wall 270. Walls 268, 270 are configured to fit within receiver 218. Saddle 250 is configured for slidable engagement with tracks 242, 246. Saddle 250 includes a concave surface 274 configured to engage at least a portion of spinal rod 152 and is moveable relative to receiver 218 in a plane, such as, for example, a sagittal plane of a body and/or vertebrae.

Saddle 250 is configured to receive and movably support spinal rod 152 such that spinal rod 152 can translate axially, rotate and/or pivot relative to receiver 218 along and about axis X3 prior to fixation with saddle 250. In some embodiments, saddle 250 defines a track 260. The surfaces that define track 260 are engageable with a pin 262 connected with receiver 218. Saddle 250 is configured for translation relative to pin 262. Pin 262 is configured to retain saddle 250 within receiver 218. Saddle 250 translates relative to receiver 218 via relative slidable translation along tracks 242, 246 such that saddle 250 is rotatable relative to receiver 218 in a plane, such as, for example, a sagittal plane of a body and/or vertebrae. Saddle 250 is rotatable about axis X3 through an angular range, as described herein. Saddle 250 is pivotable along the arcuate path of receiver 218 through rod slot 230 relative to axis X3. In some embodiments, axis X3 may be disposed at angular orientations relative to axis X2, such as, for example, acute or obtuse.

In some embodiments, saddle 250 may be elastic and pliable in a configuration to react to forces applied and/or force changes, such as, for example, positioning treatment, patient growth, trauma and degeneration, and/or component creep, deformation, damage and degeneration, to maintain the applied force transmitted from an implant positioned in rod slot 230 substantially constant. In some embodiments, saddle 250 can facilitate maintenance of a holding force on a spinal rod positioned in rod slot 230 to maintain the holding force relatively constant despite growth and changes. In some embodiments, saddle 250 may be disposed for movement in a multi axial configuration relative to receiver 218. In some embodiments, saddle 250 may be disposed in a fixed orientation relative to receiver 218.

Shaft 120 is configured to penetrate tissue, such as, for example, bone. The head or connecting portion of shaft 120 is disposed in alignment with receiver 18 such that receiver 218 is offset from shaft 120. In some embodiments, shaft 120 includes a threaded surface to facilitate engagement with tissue. In some embodiments, head 14 is monolithically formed with shaft 120. In some embodiments, head 14 is attachable, such as, for example, in a pop-on configuration with shaft 120 to form bone fastener 12. In some embodiments, head 14 is attached with shaft 120 such that bone fastener 12 comprises, for example, a sagittal angulation screw, pedicle screw, mono-axial screw, uni-planar screw, facet screw, fixed screw, tissue penetrating screw, conventional screw, expanding screw, wedge, anchor, staple, nail and/or post. In some embodiments, the head or connecting portion of shaft 120 may be alternatively aligned with intermediate portions of head 14 and/or adjacent receiver 218.

In some embodiments, spinal implant system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels.

In assembly, operation and use, spinal implant system 10, similar to the systems and methods described herein, is employed with a surgical procedure, such as, for example, a correction treatment of an applicable condition or injury of an affected section of a spinal column and adjacent areas within a body. Spinal implant system 10 may be completely or partially revised, removed or replaced.

Figure 6:
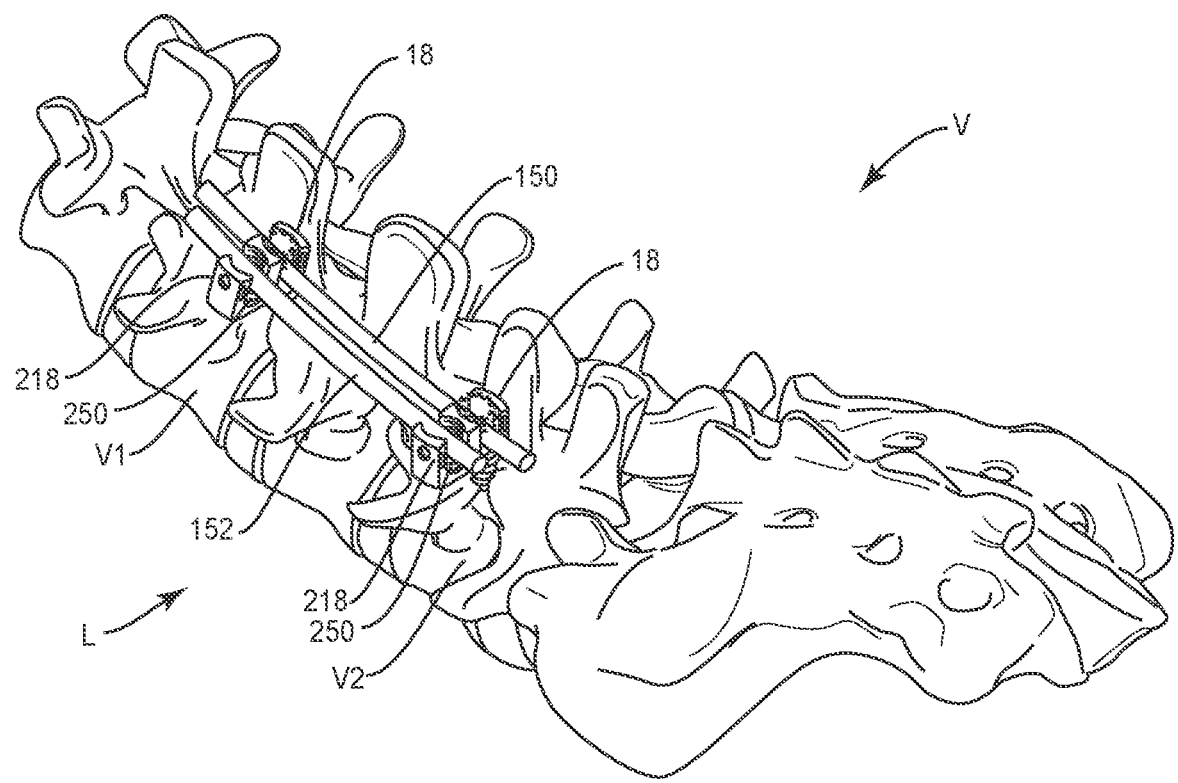
FIG. 6 is a perspective view of components of one embodiment of a system in accordance with the principles of the present disclosure disposed with vertebrae.

In use, to treat a selected section of vertebrae V, including vertebrae V1, V2, as shown in FIG. 6, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Bone fasteners 12 are engaged with vertebrae V along a lateral side L of vertebrae V. Each shaft 120 is manipulated to drive, torque, insert or otherwise connect a bone fastener 12 with vertebrae V. Spinal rod 150 is delivered along the surgical pathway to a surgical site adjacent vertebrae V. Spinal rod 150 is disposed with receiver 18 of bone fastener 12 along vertebrae V. Spinal rod 150 is manipulated to dispose spinal rod 150 with rod slot 30 from a top loading orientation.

Spinal rod 150 is fixed with receiver 18 with a set screw (not shown). The set screw is engaged with a surgical instrument, such as, for example, a driver (not shown), which advances the set screw into engagement with arm 26 and portion 28 in a locking orientation, as described herein. The driver engages the set screw to provisionally fix spinal rod 150 with receiver 18 and for attachment of spinal rod 150 with vertebrae V.

Spinal rod 152 is disposed with receiver 218 of bone fastener 12 along vertebrae V. Spinal rod 152 is manipulated to dispose spinal rod 152 with rod slot 230 and saddle 250 from a top loading orientation. Saddle 250 receives and movably supports spinal rod 152 such that spinal rod 152 is movable within rod slot 230, as described herein. Saddle 250 facilitates capture and/or orientation of spinal rod 152 by adapting to a sagittal angulation of spinal rod 152 after placement of spinal rod 150 in rod slot 30. In some embodiments, saddle 250 is selectively translatable along an arcuate path relative to receiver 218 in the sagittal plane to accommodate sagittal anatomical differences. Bone fastener 12 provides angular accommodation in a sagittal plane of vertebrae V.

Spinal rod 152 is fixed with receiver 218 with a set screw (not shown). The set screw is engaged with a surgical instrument, such as, for example, a driver (not shown), which advances the set screw into engagement with portion 226 and arm 228 in a locking orientation, as described herein. The driver engages the set screw to fix spinal rod 152 with receiver 218 and for attachment of spinal rod 152 with vertebrae V. Spinal rods 150, 152 are fixed with bone fasters 12 for attachment of spinal rods 150,152 with vertebrae V.

In some embodiments, spinal implant system 10 includes a second set of bone fasteners 12 and spinal rods 150, 152 (not shown) delivered along the surgical pathway to the surgical site adjacent a contra-lateral side of vertebrae V. The second set of bone fasteners 12 and spinal rods 150, 152 are connected with the contra-lateral side of vertebrae V, similar to lateral side L described herein. In some embodiments, the spinal constructs of spinal implant system 10, as described herein, are fixed with vertebrae V in a side by side orientation and/or a bi-lateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

Figure 7:
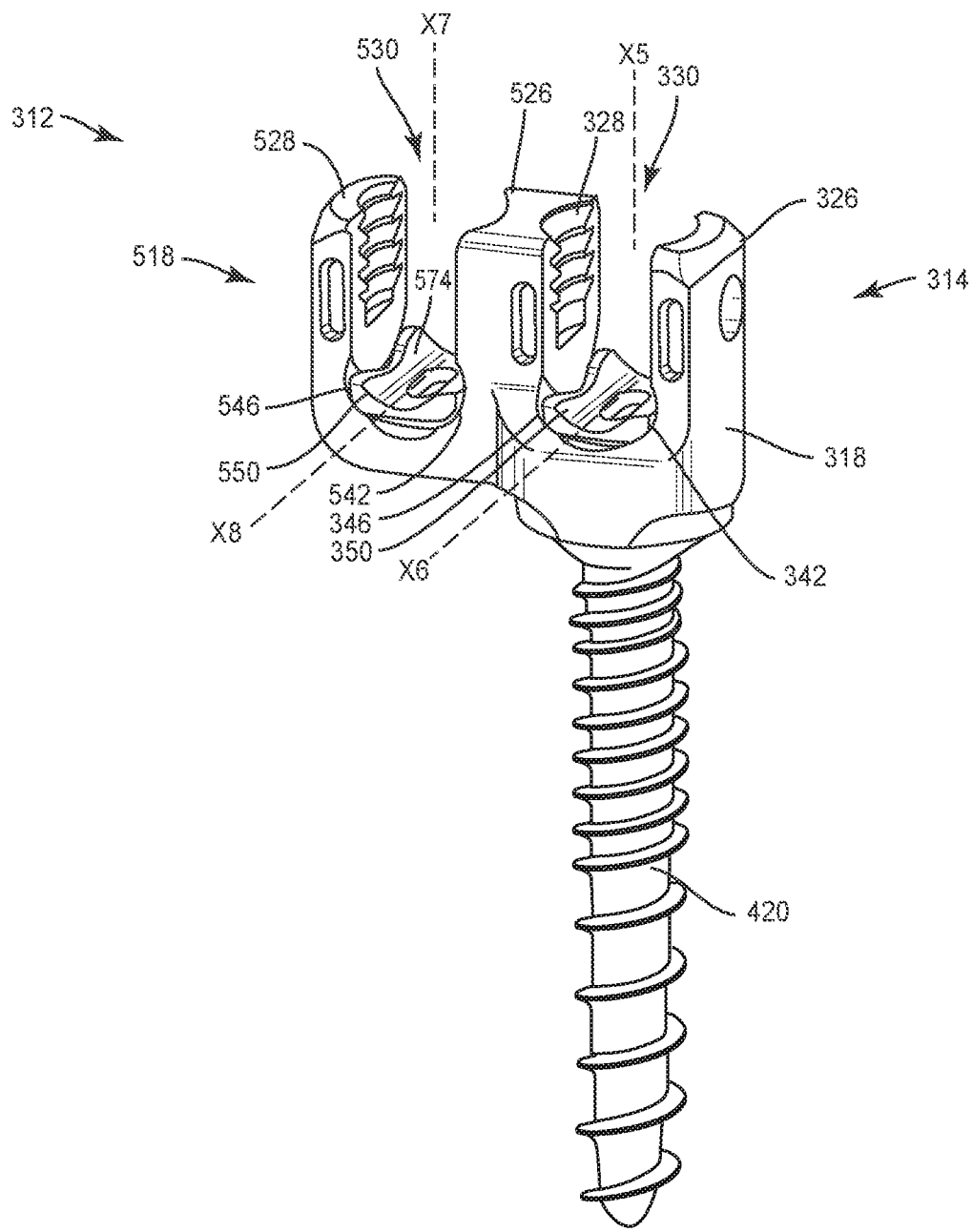
FIG. 7 is a perspective view of components of one embodiment of a system in accordance with the principles of the present disclosure.

In one embodiment, as shown in FIG. 7, spinal implant system 10, similar to the systems and methods described herein, includes a bone fastener 312. Bone fastener 312 includes a head 314 and a shaft 420, similar to head 14 and shaft 120 described herein. Head 314 is attached with shaft 420 in a fixed relative orientation.

Head 314 includes a receiver 318, similar to receiver 18 described herein. Receiver 318 is disposed in axial alignment with a head or connecting portion of shaft 420. Receiver 318 defines an axis X5 and includes an arm 326 and a portion 328 of an intermediate arm of head 314. Arm 326 and portion 328 are spaced apart to define a rod slot 330 therebetween, similar to rod slots 30, 230 described herein. Rod slot 330 is configured for top loading of a spinal rod, similar to that described herein. Arm 326 and portion 328 each extend parallel to axis X5. Rod slot 330 defines and extends along an axis X6.

Arm 326 and portion 328 are configured to support relative movement of a saddle 350, similar to saddle 250 described herein. Tracks 342, 346 facilitate translation of saddle 350 relative to receiver 318, similar to that described herein, such that saddle 350 engages a spinal rod and is moveable relative to receiver 318 in a plane of a body and/or vertebrae. Saddle 350 is configured to receive and movably support a spinal rod such that the spinal rod can translate axially, rotate and/or pivot relative to receiver 318 along and about axis X6 prior to fixation.

Head 314 includes a receiver 518, similar to receiver 18 described herein. Receiver 518 defines an axis X7, and includes a portion 526 of the intermediate arm and an arm 528. Portion 526 and arm 528 are spaced apart to define a rod slot 530 therebetween, similar to rod slots 30, 230 described herein. Rod slot 530 is configured for top loading of a spinal rod. Portion 526 and arm 528 each extend parallel to axis X7. In some embodiments, receivers 318, 518 form a ω-shaped cross section configuration of bone fastener 312. Rod slot 530 defines and extends along an axis X8.

Arms 526, 528 are configured to support relative movement of a saddle 550, similar to saddle 250 described herein. Tracks 542, 546 facilitate translation of saddle 550 relative to receiver 518, similar to that described herein, such that saddle 550 engages a spinal rod and is moveable relative to receiver 518 in a plane of a body and/or vertebrae. Saddle 550 is configured to receive and movably support a spinal rod such that the spinal rod can translate axially, rotate and/or pivot relative to receiver 518 along and about axis X8 prior to fixation.

Figure 8:
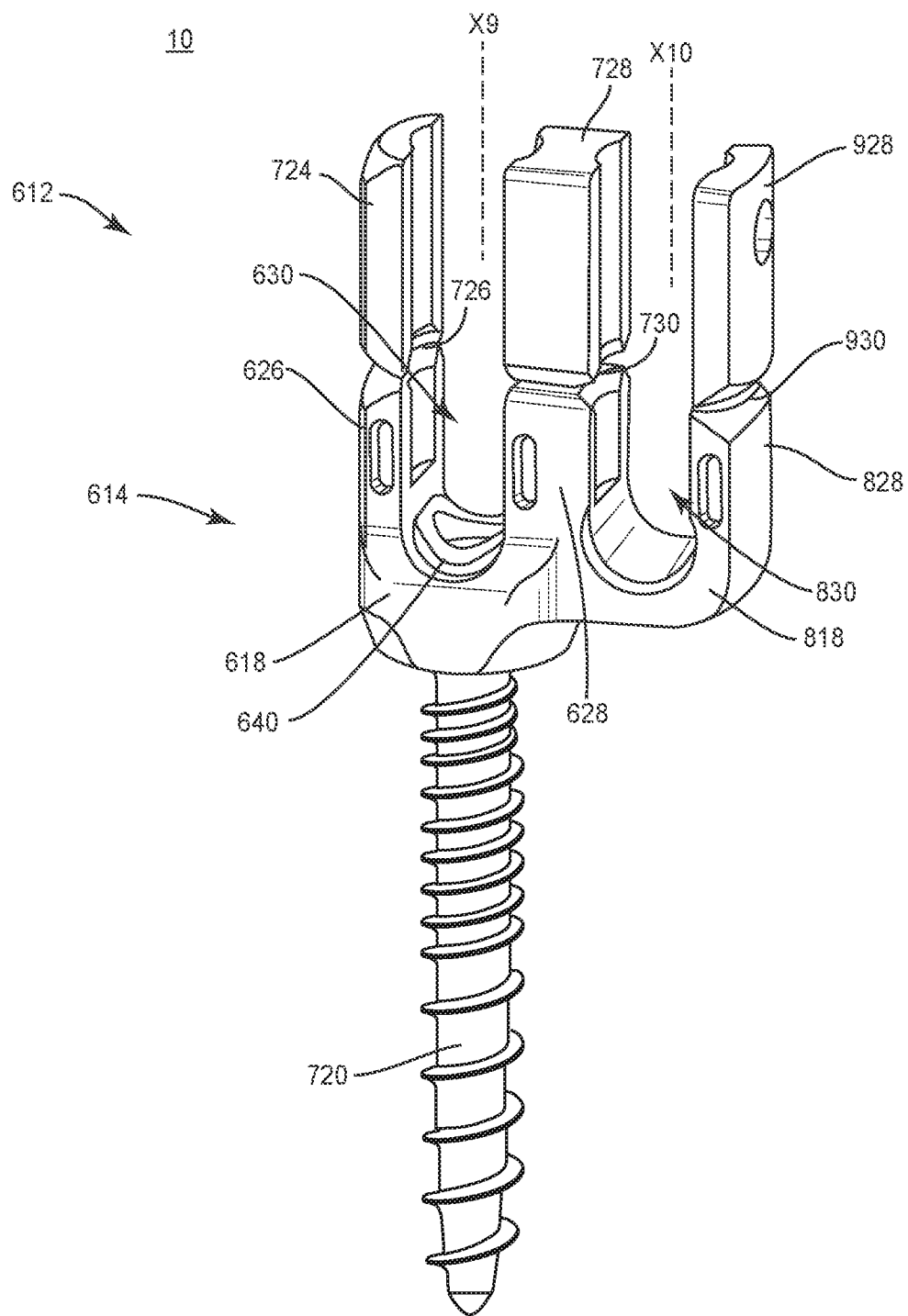
FIG. 8 is a perspective view of components of one embodiment of a system in accordance with the principles of the present disclosure.

In one embodiment, as shown in FIG. 8, spinal implant system 10, similar to the systems and methods described herein, includes a bone fastener 612, similar to bone fastener 12 described herein. Bone fastener 612 includes a head 614 and a shaft 720, similar to head 14 and shaft 120 described herein. Head 614 is attached with shaft 720 in a multi-axial screw configuration, as described herein. In some embodiments, head 614 can be attached with shaft 720 in alternate configurations, such as those described herein.

Head 614 includes arms 626, 628, 828 that define receivers 618, 818, similar to the arms and receivers described herein. Receivers 618, 818 define rod slots 630, 830, similar to the rod slots described herein, configured for disposal of spinal rods. Receiver 618 includes a crown 640, similar to crown 40 described herein. In some embodiments, receiver 618 and/or receiver 818 can include a saddle, similar to saddle 250 described herein.

Arm 626 includes a break away tab 724 that is frangibly connected to arm 626 at a portion 726. Portion 726 is fabricated from a fracturing and/or frangible material such that manipulation of tab 724 relative to arm 626 can fracture and separate tab 724 from arm 626 along portion 726 at a predetermined force and/or torque limit, as described herein. Arm 628 includes a break away tab 728 that is frangibly connected to arm 628 at a portion 730. Portion 730 is fabricated from a fracturing and/or frangible material such that manipulation of tab 728 relative to arm 628 can fracture and separate tab 728 from arm 628 along portion 730 at a predetermined force and/or torque limit, as described herein. Arm 828 includes a break away tab 928 that is frangibly connected to arm 828 at a portion 930. Portion 930 is fabricated from a fracturing and/or frangible material such that manipulation of tab 928 relative to arm 828 can fracture and separate tab 928 from arm 828 along portion 930 at a predetermined force and/or torque limit, as described herein. In some embodiments, as force and/or torque is applied to tab 724, tab 728 and/or tab 928 and resistance increases, for example, the predetermined torque and force limit is approached.

In some embodiments, tab 724, tab 728 and/or tab 928 are configured to facilitate reduction of one or more spinal rods, as described herein, with a bone fastener and/or vertebrae. Tabs 724, 728, 928 are configured to extend an overall height of bone fastener 612 and facilitate disposal of one or more spinal rods with receivers 618, 818. In some embodiments, tabs 724, 728, 928 can fracture and separate at a predetermined force or torque limit, which may be in a range of approximately 2 Newton meters (N-m) to 8 Nm. In some embodiments, tabs 724, 728, 928 and arms 626, 628, 828 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 724, 728, 928 from arms 626, 628, 828.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
a head including a first arm, a second arm and a third arm, the third arm extending at an acute angle relative to the first arm, an inner surface of the first arm and an inner surface of the second arm defining a first rod slot, an outer surface of the second arm and an inner surface of the third arm defining a second rod slot, the third arm having a length substantially equal to a length of the first arm, wherein the first arm, the second arm and the third arm are permanently fixed relative to one another;
a shaft attached with the head and configured to engage tissue;
a part movably disposed within the first rod slot such that the part engages the shaft;
a first extender coupled to the first arm; and
a second extender coupled to the second arm.

2. The bone fastener recited in claim 1, wherein the shaft is attached with the head in a multi-axial configuration.

3. The bone fastener recited in claim 1, wherein the shaft is attached with the head in a fixed angle configuration.

4. The bone fastener recited in claim 1, wherein the first rod slot is permanently fixed relative to the second rod slot.

5. The bone fastener recited in claim 1, wherein the second rod slot extends parallel relative to the first rod slot in a first plane and at the acute angle relative to the first rod slot in a second plane that extends perpendicular to the first plane.

6. The bone fastener recited in claim 1, wherein the first and second arms extend parallel to one another.

7. The bone fastener recited in claim 1, wherein the first extender is removably connected to the first arm and the second extender is removably connected to the second arm.

8. The bone fastener recited in claim 1, wherein the first extender is frangibly connected to the first arm and the second extender is frangibly connected to the second arm.

9. The bone fastener recited in claim 1, wherein the first extender is connected to the first arm at a first reduced diameter portion and the second extender is connected to the second arm at a second reduced diameter portion.

10. The bone fastener recited in claim 1, wherein a portion of the second arm extends parallel to the first arm and a portion of the second arm extends parallel to the third arm.

11. The bone fastener recited in claim 1, wherein an inner surface of the first extender is continuous with the inner surface of the first arm and an inner surface of the second extender is continuous with the inner surface of the second arm.

12. The bone fastener recited in claim 11, wherein an outer surface of the second extender is continuous with an outer surface of the second arm.

13. The bone fastener recited in claim 1, wherein the part comprises a distal end that engages the shaft and an opposite proximal end disposed within the first rod slot, the proximal end comprising a concave proximal end surface.

14. The bone fastener recited in claim 1, further comprising a third extender extending from the third arm.

15. The bone fastener recited in claim 14, wherein an inner surface of the first extender is continuous with the inner surface of the first arm, an inner surface of the second extender being continuous with the inner surface of the second arm, an outer surface of the second extender being continuous with an outer surface of the second arm and an inner surface of the third extender being continuous with the inner surface of the third arm.

16. The bone fastener recited in claim 15, wherein the inner surfaces each include a concave portion positioned between planar portions.

17. The bone fastener recited in claim 14, wherein the first extender is removably connected to the first arm, the second extender being removably connected to the second arm and the third extender being removably coupled to the third arm.

18. The bone fastener recited in claim 14, wherein the first extender is connected to the first arm at a first reduced diameter portion, the second extender being connected to the second arm at a second reduced diameter portion and the third extender being connected to the third arm at a third reduced diameter portion.

19. The bone fastener recited in claim 14, wherein:
the second and third arms extend parallel to one another; and
the first extender is coaxial with the first arm, the second extender is coaxial with the second arm and the third extender is coaxial with the third arm.

20. The bone fastener recited in claim 14, wherein the second arm is positioned between the first arm and the third arm, the second extender having a width greater than a width of the first extender and a width of the third extender.

21. The bone fastener recited in claim 14, wherein the second arm is positioned between the first arm and the third arm, the second arm having a width greater than a width of the first arm and a width of the third arm.

22. A bone fastener comprising:
a head including a first arm, a second arm and a third arm, the first and second arms extending parallel to one another, the third arm extending at an acute angle relative to the first arm, the third arm having a length equal to a length of the first arm, an inner surface of the first arm and an inner surface of the second arm defining a first rod slot, an outer surface of the second arm and an inner surface of the third arm defining a second rod slot, the first rod slot being permanently fixed relative to the second rod slot, the first rod slot extending parallel to the second rod slot, wherein the first arm, the second arm and the third arm are permanently fixed relative to one another;
a crown movably disposed within the first rod slot;
a shaft engaging the crown, the shaft being attached with the head in a multi-axial configuration;
a first extender removably coupled to the first arm such that the first extender extends parallel to the first arm and an inner surface of the first extender is continuous with the inner surface of the first arm; and
a second extender removably coupled to the second arm such that the second extender extends parallel to the second arm, an inner surface of the second extender being continuous with the inner surface of the second arm and an outer surface of the second extender being continuous with an outer surface of the second arm.

23. A bone fastener comprising:
a head including a first arm, a second arm and a third arm, the first and second arms extending parallel to one another, the third arm extending at an acute angle relative to the first arm, the third arm having a length equal to a length of the first arm, an inner surface of the first arm and an inner surface of the second arm defining a first rod slot, an outer surface of the second arm and an inner surface of the third arm defining a second rod slot, the first rod slot being permanently fixed relative to the second rod slot, the first rod slot extending parallel to the second rod slot, wherein the first arm, the second arm and the third arm are permanently fixed relative to one another;
a crown movably disposed within the first rod slot;
a shaft directly engaging the crown, the shaft being attached with the head in a multi-axial configuration;
a first extender removably coupled to the first arm such that the first extender extends parallel to the first arm and an inner surface of the first extender is continuous with the inner surface of the first arm;
a second extender removably coupled to the second arm such that the second extender extends parallel to the second arm, an inner surface of the second extender being continuous with the inner surface of the second arm and an outer surface of the second extender being continuous with an outer surface of the second arm; and
a third extender removably coupled to the third arm such that the third extender extends parallel to the third arm and an inner surface of the third extender is continuous with the inner surface of the third arm.

* * * * *